(12) United States Patent
Shelton

(10) Patent No.: US 8,215,957 B2
(45) Date of Patent: Jul. 10, 2012

(54) DENTAL IMPLANT PLACEMENT LOCATOR AND METHOD OF USE

(76) Inventor: Robert Shelton, Longview, TX (US)

( * ) Notice: Subject to any disclaimer, the term of this patent is extended or adjusted under 35 U.S.C. 154(b) by 589 days.

(21) Appl. No.: 11/127,510

(22) Filed: May 12, 2005

(65) Prior Publication Data

US 2006/0257817 A1 Nov. 16, 2006

(51) Int. Cl.
*A61C 3/00* (2006.01)
(52) U.S. Cl. .................................................. 433/75
(58) Field of Classification Search ............ 433/72–76, 433/34, 50, 55–56, 172–176, 213–214, 229; 623/167, 1.38, 1.34; 378/162–164; 606/96
See application file for complete search history.

(56) References Cited

U.S. PATENT DOCUMENTS

| | | | | |
|---|---|---|---|---|
| 3,547,121 A | * | 12/1970 | Cherry | 604/116 |
| 4,642,096 A | * | 2/1987 | Katz | 604/116 |
| 4,837,795 A | * | 6/1989 | Garrigus | 378/180 |
| 5,015,183 A | | 5/1991 | Fenick | |
| 5,105,457 A | * | 4/1992 | Glassman | 378/163 |
| 5,320,529 A | * | 6/1994 | Pompa | 433/76 |
| 5,409,493 A | | 4/1995 | Greenberg | |
| 5,415,546 A | | 5/1995 | Cox, Sr. | |
| 5,613,852 A | * | 3/1997 | Bavitz | 433/173 |
| 5,669,915 A | | 9/1997 | Caspar et al. | |
| 5,718,579 A | * | 2/1998 | Kennedy | 433/75 |
| 5,746,743 A | | 5/1998 | Greenberg | |
| 5,769,637 A | * | 6/1998 | Morgan | 433/176 |
| 5,775,900 A | | 7/1998 | Ginsburg et al. | |
| 5,800,526 A | * | 9/1998 | Anderson et al. | 623/1.16 |
| 5,848,125 A | * | 12/1998 | Arnett | 378/162 |
| 5,851,207 A | | 12/1998 | Cesarone | |
| 5,888,034 A | | 3/1999 | Greenberg | |
| 5,897,696 A | | 4/1999 | Giordano et al. | |
| 5,954,769 A | | 9/1999 | Rosenlicht | |
| 6,045,565 A | * | 4/2000 | Ellis et al. | 606/167 |
| 6,340,367 B1 | * | 1/2002 | Stinson et al. | 623/1.34 |
| 6,382,975 B1 | | 5/2002 | Poirier | |
| 6,928,146 B2 | * | 8/2005 | Broyles et al. | 378/164 |
| 7,086,860 B2 | * | 8/2006 | Schuman et al. | 433/75 |
| 7,097,451 B2 | * | 8/2006 | Tang | 433/76 |
| 7,108,716 B2 | * | 9/2006 | Burnside et al. | 623/1.38 |
| 2001/0020184 A1 | * | 9/2001 | Dehdashtian et al. | 623/1.16 |
| 2002/0095205 A1 | * | 7/2002 | Edwin et al. | 623/1.13 |
| 2004/0166462 A1 | | 8/2004 | Phan et al. | |
| 2004/0219480 A1 | * | 11/2004 | Malin | 433/75 |
| 2005/0004581 A1 | * | 1/2005 | Astrom | 606/130 |

(Continued)

*Primary Examiner* — Cris L Rodriguez
*Assistant Examiner* — Hao D Mai
(74) *Attorney, Agent, or Firm* — Schultz & Associates, P.C.

(57) ABSTRACT

The present invention provides a device and method for facilitating the placement of dental implants by use of an implant placement locator and a sequentially sized drill orientation tube series. The implant placement locator disclosed herein comprises a visible radiolucent moldable grid, a set of radiopaque markers located at known intervals within the moldable grid, and a plastic sheeting encasing the visible radiolucent moldable grid and the radiopaque markers. The method of the present invention comprises obtaining a radiograph of a patient's mouth with the implant placement locator overlaying the patient's dental ridge and then transferring reference points as indicated by the location of the radiopaque markers relative to existing teeth and other oral structures to a dental stone model. In a preferred embodiment, drill bits are directed in the desired trajectory into the patient's available lower or upper jaw bone by use of drill orientation tubes in combination with the implant placement locator. A sequentially sized set of spacers is provided having sequentially sized inside diameters to direct varying diameter drills. Drill guide parallelism is thus provided by the invention.

35 Claims, 5 Drawing Sheets

U.S. PATENT DOCUMENTS

2005/0037320 A1* 2/2005 Poirier .......................... 433/173
2006/0251220 A1* 11/2006 Young et al. ................... 378/204
2006/0281046 A1* 12/2006 Heo ................................ 433/75

* cited by examiner

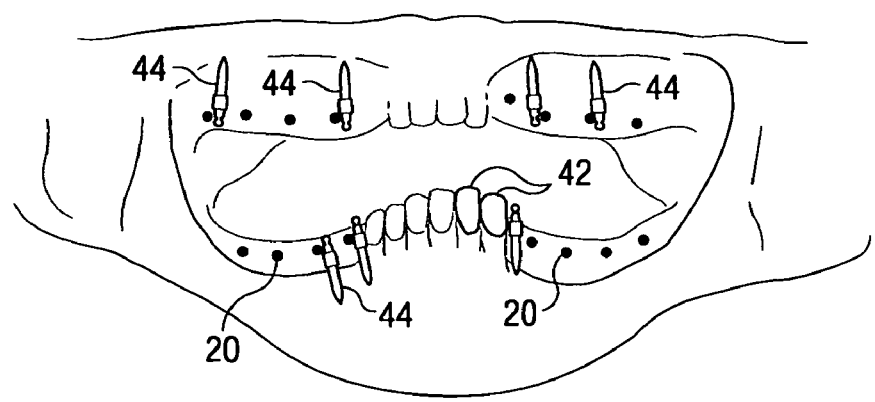
FIG. 10
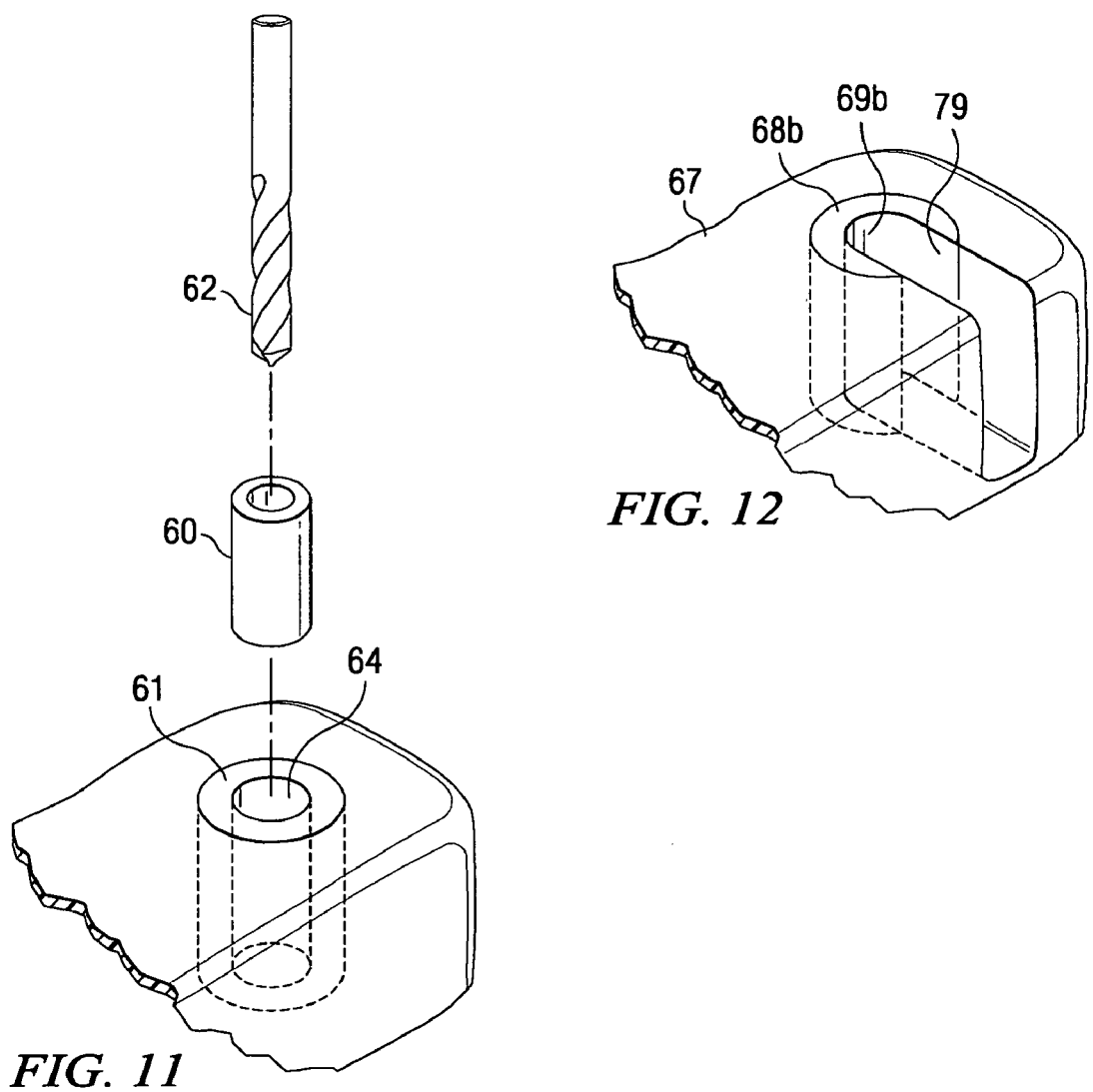
FIG. 11
FIG. 12 ic DENTAL IMPLANT PLACEMENT LOCATOR
AND METHOD OF USE

FIELD OF THE INVENTION

The present embodiments relate to a device and method for indexing radiographic locations of dental structures to markers to facilitate implant surgery and placement of dental implants. The present embodiments further relate to a device and method for directing a drill bit to a specific drill site and angle for the placement of dental implants.

BACKGROUND OF THE INVENTION

Devices and methods for fabricating dental templates, utilizing radiopaque substances in connection with dental stents and manufacturing dental implant structures are disclosed in the following: U.S. Application No. 2004/0166462 A1 to Phan, U.S. Pat. No. 5,897,696 to Giordano, U.S. Pat. No. 5,415,546 to Cox, and U.S. Pat. No. 6,382,975 B1 to Poirier. Difficulties encountered in the placement of dental implants include maintaining the accuracy of placements and efficiently utilizing evidence of bone available for surgical drilling.

Surgical drills are typically used during dental implant surgery in order to achieve the placement of dental implants. Related patents include U.S. Pat. Nos. 5,409,493, 5,746,743, and 5,888,034 to Greenberg. Difficulty in maintaining a parallel orientation of the varying drill sizes throughout the implantation process is a common problem encountered during dental implant procedures.

The dental implant locator of the present invention is made for use in facilitating placement of implants relative to radiographic determinations of available bone structures relative to the oral tissues of the mouth. The dental implant placement locator disclosed overcomes the difficulty typically encountered in achieving an accurate placement of dental implants and in positioning drills during oral surgery.

BRIEF DESCRIPTION OF THE DRAWINGS

In the detailed description of the preferred embodiments presented below, reference is made to the accompanying drawings.

FIG. 10 is a panoramic radiograph of a patient's mouth showing the final placement of dental implants with the implant placement locator in place.

FIG. 11 is an exploded view of the drill guide, drill bit spacer and drill bit.

FIG. 12 is an expanded view of an alternate embodiment of the drill guide.

The present embodiments are detailed below with reference to the listed Figures.

DETAILED DESCRIPTION OF THE PREFERRED
EMBODIMENTS

Before explaining the present embodiments in detail, it is to be understood that the embodiments are not limited to the particular descriptions and that the embodiments can be practiced or carried out in various ways.

Figure 1:
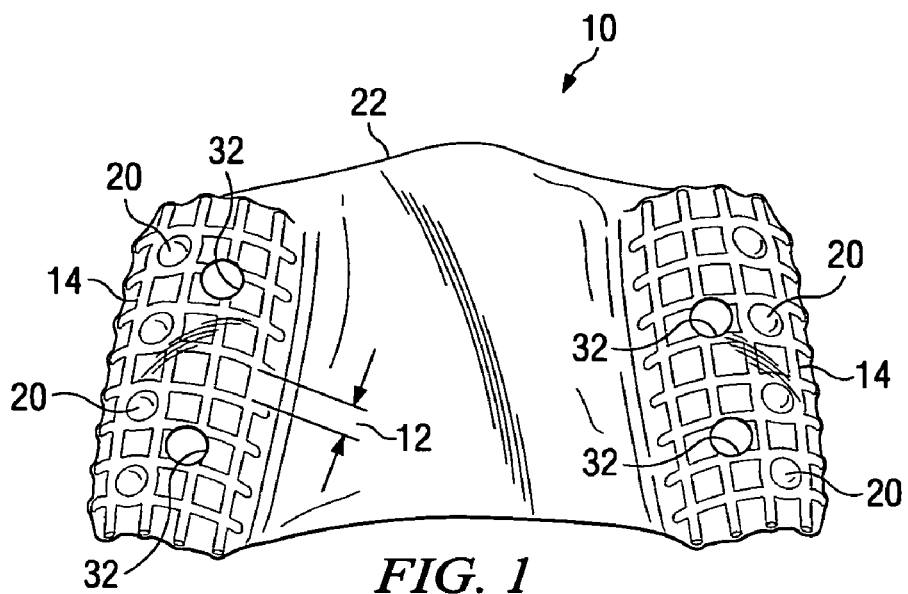
FIG. 1 is a perspective view of a preferred embodiment of an implant placement locator.

The implant placement locator of the present invention is seen in FIG. 1 and is generally referred to by reference number 10.

Implant placement locator 10 is comprised of visible or visibly opaque moldable grid 14 having grid spacing 12, radiopaque markers 20 located at indexed intervals on moldable grid 14, and plastic sheeting 22 which encases moldable grid 14 and radiopaque markers 20.

Figure 2:
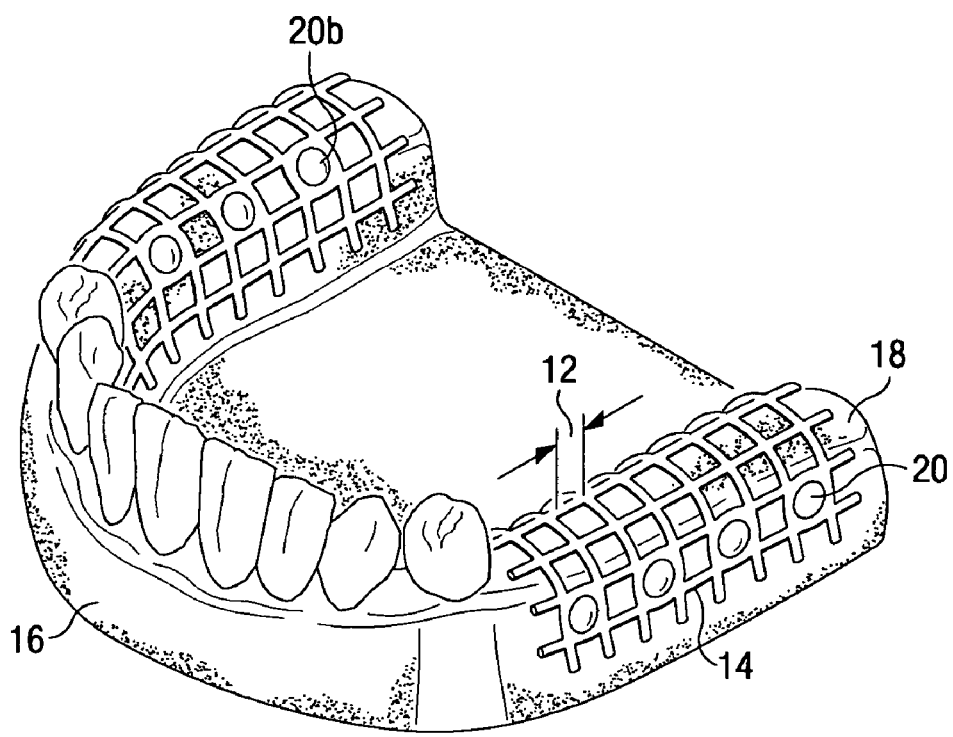
FIG. 2 is an isometric view depicting the moldable grid formed onto a dental stone model and radiopaque markers located at known intervals on the moldable grid.
Figure 4:
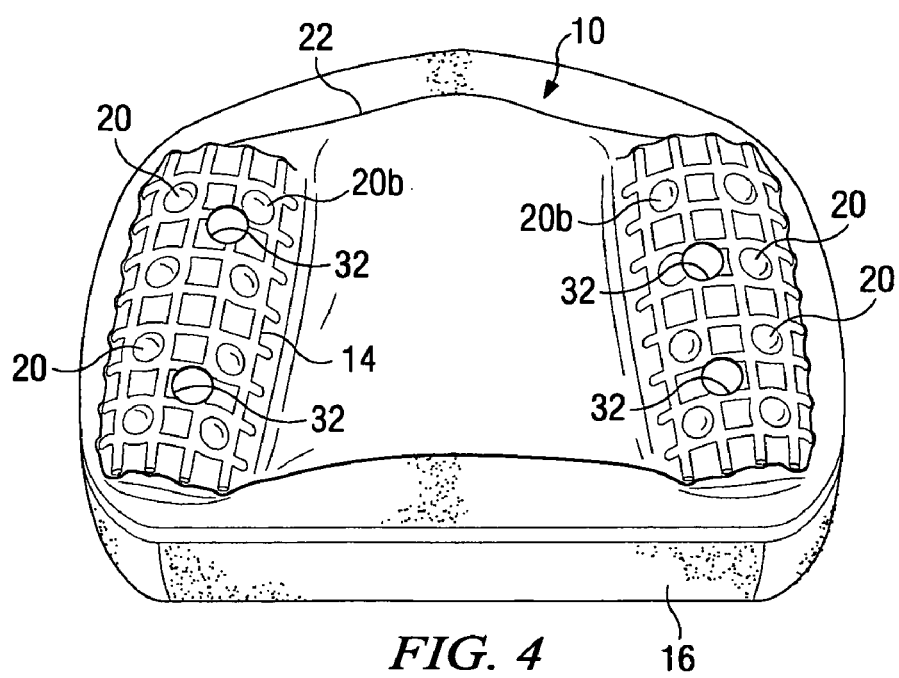
FIG. 4 is a perspective view depicting the implant placement locator on a dental stone model.

Implant placement locator 10 is designed to be placed in the patient's mouth in a variety of configurations, as required for a particular dental implant procedure. Referring to FIG. 2, in one embodiment, moldable grid 14 of implant placement locator 10 can cover the right or left dental ridge 18 on the upper or lower jaw, also respectively described as the maxilla or mandible, of a patient. In another embodiment, moldable grid 14 may cover both the right and left dental ridge 18 in addition to dental ridge 18 corresponding to the patient's front teeth on the upper or lower jaw. In yet another embodiment, moldable grid 14 may cover the entire dental palate of a patient. Referring to FIG. 1 and FIG. 4, implant placement locator 10 is shown having dental implant sites at four locations on implant placement locator 10. Each dental implant site is designated by drill hole 32 in moldable grid 14 and plastic sheeting 22 of implant placement locator 10.

The moldable grid 14 can be radiotransparent or radiolucent and visibly opaque. When visibly opaque, the grid can be easily seen on the dental model or when in use in the oral cavity. When radiotransparent or radiolucent, no grid is seen in the radiograph. The grid shape of the preferred material for moldable grid 14 is square. The size of the open spaces of the grid (grid spacing) is between about 1 and about 5 millimeters with the preferred grid spacing being 2 millimeters. Other shapes and dimensions of the grid spacing can accommodate different applications. For instance, hexagonal or rectangular spacing may be used where applied angle of the grid relative to the radiograph is such that the square spacing would not be useful. In an alternate embodiment, moldable grid 14 can be formed from a plastic which is curable in ultraviolet light.

In an alternative embodiment, the moldable grid has molded within it a thin flexible radiopaque wire. In this embodiment the wire is visible as a white pattern in the radiograph allowing the grid to be used as a scale and index relative to bone structures and the markers.

Radiopaque markers 20 are located at indexed or known intervals within grid spacing 12 of moldable grid 14, as can be clearly seen in FIG. 1 and FIG. 2. The markers may be placed anywhere in the grid. For example, the markers are shown to be placed outside the dental ridge or the buccal side in FIG. 2 and on top of the dental ridge in FIG. 1. Also shown in FIG. 2-4 at 20b, the markers may be placed on the buccal, lingual and palatal surfaces Radiopaque markers 20 provide reference points for radiographic determination of available bone (or other identifiable dental structure) relative to a particular oral tissue or marker location for surgical planning or at the time of dental implant surgery. Radiopaque markers 20 are preferably inert metallic spheres ranging in size from about 1 mm to about 5 mm. In a preferred embodiment, radiopaque markers 20 are formed from 3 mm stainless steel balls, which can be easily sterilized. Of course, other shapes such as cubes or tetrahedrons may be used as well, alone or in combination with other shapes. "Coding" or identifying dental structures through use of a combination of shapes of the radiopaque markers is also possible. Radiopaque markers 20 are held in place by a pressure fit in grid spacing 12 of moldable grid 14, grid spacing 12 being locally deformed to accept the shape of radiopaque markers 20. Plastic sheeting 22 is bonded to radiopaque markers 20 and moldable grid 14 by melting of plastic sheeting 22 around radiopaque markers 20 and moldable grid 14. Plastic sheeting 22 therefore adheres to the radiopaque markers through a deformation that flows into moldable grid 14 upon heat treatment and vacuum formation of plastic sheeting 22.

Alternatively, radiopaque markers 20 may be held in place by an adhesive which secures the markers in the interstices of grid spacing 12. Epoxies and adhesives known for use in a dental environment can be used.

In the preferred embodiment, plastic sheeting 22 is approximately 1 millimeter thick and transparent. The thickness of plastic sheeting 22 can vary between about 1 millimeter and about 5 millimeters, depending on the rigidity of the final structure desired. Transparency of the plastic sheeting 22 allows for location of various bone structures 41 and tooth structures 42 during use. Location of various features of a stone model used during surgical planning is also enhanced by the transparency of plastic sheeting 27. In an alternate embodiment, plastic sheeting 22 may be an optically shaded material. For example, clear colored and transparent colored plastic sheeting can be used to identify implant placements and placement locators with respect to a particular patient or surgical process.

Figure 3:
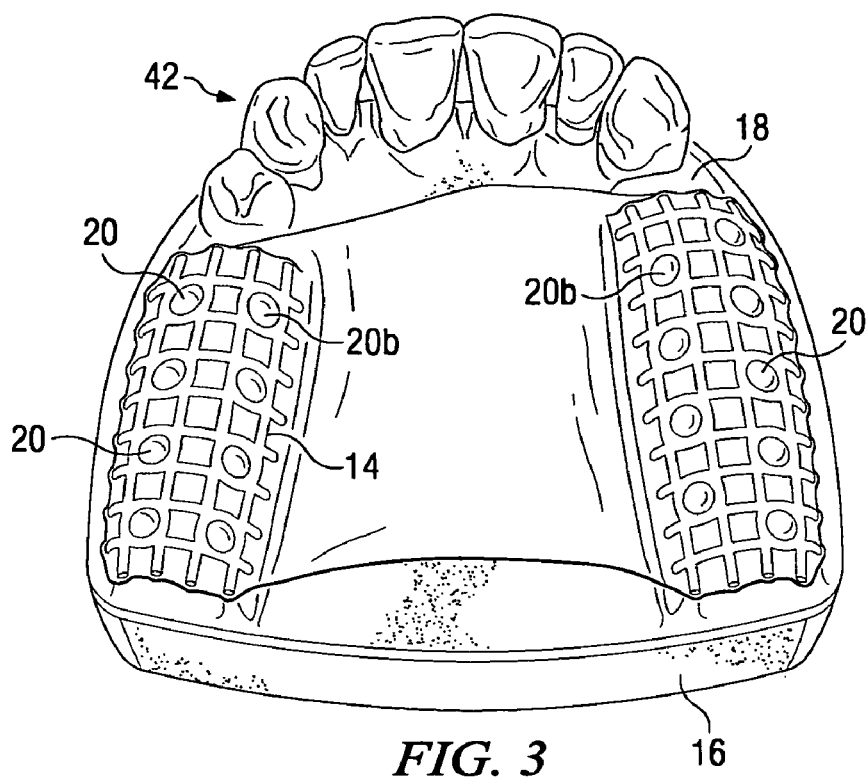
FIG. 3 is a perspective view depicting the placement of radiopaque markers on a dental stone model of the upper jaw.

FIG. 2, FIG. 3, and FIG. 4, depict fabrication steps of implant placement locator 10 on dental stone model 16. FIG. 2 shows dental stone model 16 with an implant placement locator in place. The material for moldable grid 14 is first cut to fit the areas of interest on the dental stone model. Moldable grid 14 is then placed on dental stone model 16. For example, FIG. 2 shows moldable grid 14 placed in a "saddle" type fashion over the left and right side of dental ridge 18. The moldable grid 14 can also extend across the entire dental palate of a patient as in FIG. 6.

Application of heat to moldable grid 14 causes it to soften and become molded to the contours of dental stone model 16. A heat gun may be used to supply the required temperature for softening. Radiant heat sources such as infrared lights may be used as well. Upon cooling, moldable grid 14 becomes rigid as it overlays dental stone model 16. In an alternate embodiment, moldable grid 14 can be molded and then cured by ultraviolet light while on dental stone model 16.

Once moldable grid 14 has become rigid, radiopaque markers 20 are placed at indexed intervals in grid spacing 12 of moldable grid 14 as moldable grid 14 overlays dental stone model 16 of a patient's mouth, as shown in FIG. 2. In another embodiment, radiopaque markers 20 can be placed at indexed intervals in grid spacing 12 of moldable grid 14 as moldable grid 14 overlays dental stone model 16 of the maxilla or upper jaw of a patient, as shown in FIG. 3. In an alternate embodiment, radiopaque markers 20 can be placed at a location on moldable grid 14 corresponding to a patient's tooth sockets.

Radiopaque markers 20 are stabilized within grid spacing 12 of moldable grid 14 by softening the moldable grid 14 through application of heat localized to placement of the radiopaque markers 20. In the preferred embodiment, a 20 watt soldering iron is used to provide localized heat. Alternatively, an electric or propane torch can be used with a gas tip, as will other heat sources adapted to localized heat application. The radiopaque markers 20 are then pressed into the moldable grid 14 with sufficient force to spread the moldable grid 14 around the radiopaque markers 20 in conformance with the outer surface of the radiopaque markers 20. Once allowed to cool, the radiopaque markers 20 are held in place by the moldable grid 14, locally deformed to accept the shape of the radiopaque markers 20. If an ultraviolet light curable plastic is used for moldable grid 14, the markers are pressed into place before application of ultraviolet light and curing of the plastic to rigid form.

Plastic sheeting 22 is then molded to the contours of moldable grid 14 and other desired oral structures on the stone model not covered by moldable grid 14. The plastic sheeting 22 in the preferred embodiment setting is a transparent thermoplastic capable of being deformed while heated. In this process, the plastic sheeting 22 is cut to overlap moldable grid 14, radiopaque markers 20, and the dental stone model 16. The plastic sheeting 22 is heated and manually conformed to the dental stone model 16, the moldable grid 14, and the radiopaque markers 20. The plastic sheeting 22 is then allowed to cool. After cooling, the conformance of the plastic sheeting 22 holds the moldable grid 14 and radiopaque markers 20 in place, forming a unitary and rigid yet pliable structure.

In an alternative embodiment, plastic sheeting 22 is heated and then drawn over moldable grid 14, radiopaque markers 20, and the dental stone model 16 through a vacuum forming process. In the vacuum forming process, a stone model is provided that is porous enough to allow the passage of the vacuum. A vacuum is then drawn on the stone model, allowing atmospheric pressure to compress the plastic sheeting 22 against the dental stone model 16, moldable grid 14, and radiopaque markers 20. Upon cooling, the vacuum is released and the rigid structure of the implant placement locator 10 is achieved.

In a preferred embodiment, a small amount of acrylic powder and resin, is applied to radiopaque markers 20 upon placement of radiopaque makers 20 within grid spacing 12 of moldable grid 14 in order to prevent movement of radiopaque markers 20 from the desired location on moldable grid 14 upon heat treatment or vacuum forming of plastic sheeting 22. In the preferred embodiment, the acrylic powder and resin mixture is well known in the art. A light cured composite as known in the art may also be used, as may a cyanoacrylate adhesive.

Figure 7:
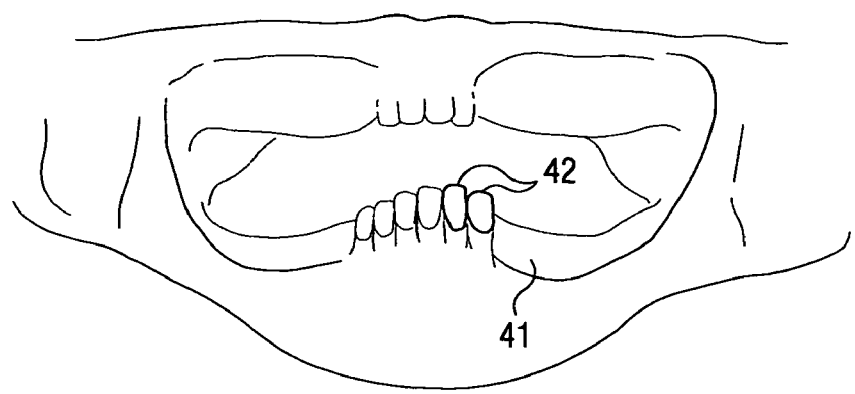
FIG. 7 is a panoramic radiograph of a patient's mouth without the implant placement locator in place, the radiograph showing the location of bone structures, including existing teeth.
Figure 8:
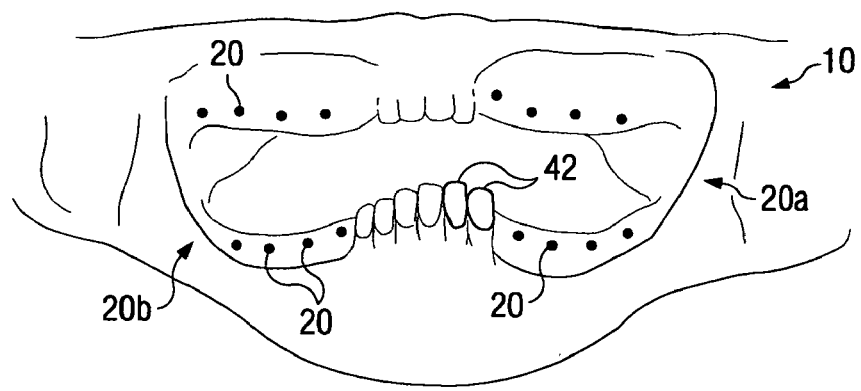
FIG. 8 is panoramic radiograph of a patient's mouth showing the implant placement locator in place and providing reference points for identifying dental implant sites by relating radiopaque markers to various oral anatomical structures.

In a preferred embodiment, the method of the present invention facilitates the placement of dental implants by following a series of steps. Implant placement locator 10, is placed over a patient's dental ridge 18. Implant placement locator 10 is held in place in the patient's mouth by fitting the implant placement locator 10 over existing teeth or other dental structures. A radiograph is then obtained of the patient's mouth with implant placement locator 10 in place. FIG. 7 shows a radiograph taken of a patient's mouth without implant placement locator 10 in place. In contrast, FIG. 8 shows a radiograph taken with implant placement locator 10 in place in the patient's mouth showing the location of radiopaque markers 20 relative to existing bone and tooth structures 42.

Implant placement locator 10 is then transferred from the patient's mouth to dental stone model 16 as seen in FIG. 4. Once on dental stone model 16, the implant placement locator allows surgical planning by correlating the location of bone structures 41 tooth structures 42 and tissue structures relative to moldable grid 14 and radiopaque markers 20. For example, a certain tissue or marker might be 2 grid spacings in one direction and 2 to 3 grid spacings in another, as judged from a subsurface bone structure shown in the radiograph. The absolute location of the markers in the uniform grid spacing makes judging distances far more accurate than is possible without the use of the invention.

Figure 9:
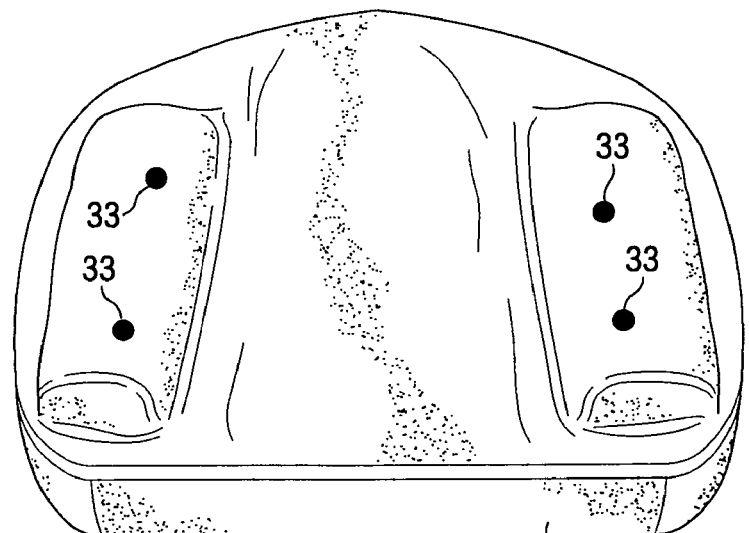
FIG. 9 is a perspective view depicting identified dental implant sites marked on a dental stone model, as determined by reference to the radiopaque markers on the implant placement locator.

Returning to FIG. 4, reference to the dental stone model allows indexing of implant locations relative to the height of the dental ridge and other considerations visible from the dental stone model. In planning, dental stone model 16 can be marked as shown in FIG. 9 with potential locations for implants shown as 33. The potential implant locations are then transferred to the implant placement locator by drilling holes through the locator corresponding to the potential implant locations. As seen in FIG. 4, rigid implant locations marked 33 on FIG. 9 correspond to drill holes 32.

Implant placement locator 10 is then transferred back into the patient's mouth and the desired dental implant site is marked on the tissue surfaces of the patient as indicated by the location of drill hole 32 in implant placement locator 10. In the preferred embodiment, the implant placement locator 10 is then removed from the patient's mouth and surgical holes are drilled based on the markings placed on the tissue surfaces of the patient. In an alternate embodiment, the implant placement locator may be left in place in the oral cavity during the surgical procedure to more accurately locate positions for the surgical holes.

During certain surgical procedures it is necessary to control the angle of or maintain parallelism between the holes drilled for the location of the dental implants. An alternate embodiment of the present invention includes a device for guiding the angle of the holes drilled pursuant to drill holes 32.

Figure 5:
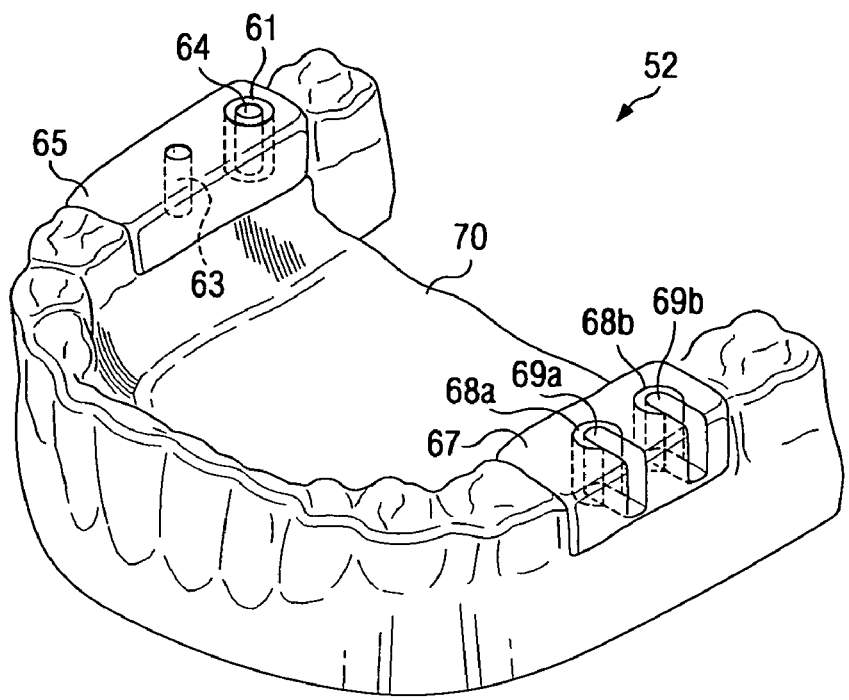
FIG. 5 is a perspective view depicting an alternate embodiment of the implant placement locator and drill guide.

FIG. 5 shows an alternative embodiment of the invention known as a surgical guide. Surgical guide 52 is a pliable plastic formed to match a patient's teeth and dental structures in either or both of the upper or lower jaw. Surgical guide 52 includes plastic sheeting 70, block material 65, a number of holes (an example is shown at 63) hole 63, and drill guide 61. Plastic sheeting 70 in the preferred embodiment is a transparent thermoplastic about 1 mm to about 5 mm thick. The plastic sheeting can be shaped to follow the dental ridge, a single side of the dental ridge or extended to cover the space between them, depending on the need in any particular surgical situation. Surgical guide 52 includes block material 65. In the preferred embodiment, block material 65 can be visible light cured plastic or an acrylic powder and resin mixture. The block in the preferred embodiment is transparent. Transparency allows light to be directed toward and illuminate the surgical area through the block. The transparency also allows visible inspection of the area on which surgery is performed. In practice, block material 65 is shaped to fit within an interstitial gap created by missing teeth. In this preferred embodiment, block material 65 includes a hole 63 of appropriate diameter to match a drill bit or outer diameter of a drill bit spacer (which will be described further later). Drill guide 61 is concentrically fixed within hole 64 on surgical guide 52 at an angle dictated by surgical considerations. Drill guide 61 is secured within the hole by an adhesive such as epoxy, cyanoacrylate or acrylic powder and resin. The adhesive rigidly maintains drill guide 61 in a position relative to surgical guide 52.

Drill guide 61 is a rigid nylon or plastic tubing. Other rigid plastic tubing can be used, such as Teflon, polyethylene or polyvinyl chloride. In one embodiment, the tubing can be radiopaque by a coating of barium or incursion of powderized barium in the plastic of the tubing. Alternately, a metal tube can be used. The tubing is generally cylindrical having an inside diameter 64 ranging from about 1 millimeter to about 10 millimeters with a preferred range of 1.6 to 5.5 millimeters. The inside diameter 64 in the drill guide also matches the outside diameter of a drill bit to be used in the surgical procedure. The outer diameter of drill guide 61 in the preferred embodiment can range from 3 millimeters to 12 millimeters with a preferred range of between 5 millimeters to 7 millimeters. The length of drill guide 61 can range between about 2 millimeters and about 15 millimeters with a preferred range of between about 3 millimeters and about 5 millimeters. The drill guide may extend above the surface of block 65 if required for stability in a given surgical procedure. As will be appreciated by those skilled in the art, the precision of the angle which is maintained during drilling increases with the length of the drill guide. All dimensions are approximate and slight variations are acceptable.

Drill bit spacer 60 is used in association with drill guide 61 and a drill bit 62 and is shown in FIG. 11. FIG. 11 illustrates a drill orientation guide 61, drill bit spacer 60 and drill bit 62 in an exploded view. Drill bit 62 fits concentrically within drill bit spacer 60 which in turn fits concentrically within drill orientation guide 61 in the preferred embodiment. Drill bit spacer 60 is formed from a rigid nylon or plastic tubing. In an alternative embodiment the plastic tubing may include a radiopaque material or be made of a metal. The outer diameter of drill bit spacer 60 must be smaller than the inner diameter of drill guide 61 by sufficient clearance to allow drill bit spacer 60 to slide axially and rotate within drill guide 61. However, the clearance cannot allow a significant variation between the axis of the drill guide 61 and the axis of the drill bit spacer 60 when the spacer is inserted in the drill guide. In the preferred embodiment, the clearance between the inner diameter of drill guide 61 and the outer diameter of drill bit spacer 60 is approximately 0.1 mm.

The length of drill bit spacer 60 in the preferred embodiment is generally the same as that of drill guide 61. But the length of the spacer may be shorter or longer than the drill guide as required for the surgical procedure.

In the preferred embodiment, there is a series of drill bit spacers. The outer diameter of each drill bit spacer is designed to fit within the inside diameter of drill guide 61 within the clearance previously described. However, the inside diameter of the drill bit spacers is different. The inside diameter of each of the drill bit spacers in the series is sequentially larger. The inside diameters are sized to accommodate a series of drill bits having sequentially increasing diameters. In the preferred embodiment, the inside diameter of each drill bit spacer in the series can range between about 2 and about 5 mm with a preferred range between about 2.2 and 4.2 mm. The sequentially sized drill bits preferably range in diameter from about 2 millimeters to about 5 millimeters.

Any number of drill guides can be positioned in surgical guide 52 at any position or angle along or above the dental ridge. In the preferred embodiment, parallelism is maintained between each of the holes and drill guides in the surgical guide in order to maintain parallelism between the resulting holes in the patient's bone after the surgical procedure. For example, hole 63 along with drill guide 61 are fixed within surgical guide 52 such that their axes are generally parallel. Parallelism between the resulting holes allows dental fixtures, such as false teeth, to be easily attached to implants. In another embodiment, the drill guide 61 and hole 63 are fixed in surgical guide 52 such that their axes are directed toward a dental implant site but are not generally parallel. In this embodiment, the implant site is targeted at a supporting bone structure relatively distant from the hole entry point.

In FIG. 5, surgical guide 52 also includes alternate drill guides 69a and 69b with inside diameters 68a and 68b, respectively and block material 67. Alternate drill guide 68b is shown in detail in FIG. 12. Alternate drill guide 68b has a slot 79 which extends through the wall of block material 67. The width of slot 79 corresponds generally to the diameter of inside diameter 69b. The purpose of the slot is to allow horizontal insertion of the drill into the drill guide. Slot 79 allows operation in confined spaces such as those found in association with surgical procedures on back teeth at the back of the jaw. Alternate drill guides 68a and 68b are parallel to drill guides 61 and hole 63 in this embodiment.

The preferred method for fabricating surgical guide 52 is as follows: Plastic sheeting 70 is cut to match the shape of dental ridge 18 or other dental structure on a dental stone model and heated. Sheeting 70 is then pressed into its desired shape around the features of the dental stone model. Sheeting 70 is then allowed to cool. Block material can be added underneath or on top of plastic sheeting 70 and is formed by using a moldable dental acrylic sized to fit within and interstitial space in the stone model. The block material is bonded to the plastic sheeting 70 with an epoxy, additional acrylic adhesive or acrylic power and resin. The required holes are then drilled through plastic sheeting 70 and into block material 65.

In the case of hole 63, the diameter is sized to be approximately the same as the drill bit which would be used during a surgical procedure. The outside diameter of hole 64 is sized to accommodate the outside diameter of drill guide 61. In an alternative method of fabrication, the block material may be formed around a drill guide held in place by a paralleling jig. Drill guide 61 is then fixed within the hole using a suitable epoxy or acrylic adhesive. During drilling of the holes, parallelism can be maintained to a general degree by using a dental drill. If a higher degree of parallelism is required, a drill press, jig or device as known in the art can be used to maintain a near exacting parallelism between the axis of each of the holes.

In another preferred embodiment, the axis of the holes may be slanted with respect to each other or the dental ridge in order to accommodate location of bone or other dental structures required for dental implant placement.

In use, surgical guide 52 is placed in the oral cavity. If the drill guide is radiopaque, radiographics may be taken to locate the drill guide with respect to dental features. A series of holes is then drilled concentrically in the bone structure, starting with the smallest diameter and ending with the largest diameter required for the surgical procedure. In order to guide the holes, drill bit spacers of various inside diameters cooperate with the drill guide and a series of differently sized drill bits to place the holes where desired to achieve a correct hole diameter and angle (or parallelism) with respect to the dental ridge. In a preferred embodiment, a series of four drill bits is used with three corresponding drill bit spacers to drill an initial hole, two intermediate sized holes and a final sized hole.

In practice, the drill bit spacer with the smallest inside diameter is chosen to match the drill bit for the lead hole. A lead hole is then drilled by the smallest diameter drill bit. After the lead hole is drilled, the smallest drill bit is removed along with the smallest diameter drill bit spacer. The drill bit spacer with the next larger inside diameter is then placed on a drill bit with a larger inner diameter which corresponds to the desired larger hole. The next larger drill bit, along with the next larger drill bit spacer is then placed and centered within drill guide 61 to drill a larger lead hole. The drill bit spacers rotate within the drill guides. This process is then repeated for each drill guide and drill bit spacer until all desired holes are drilled at all desired diameters. In the preferred embodiment, the outer diameter of the largest and final drill bit corresponds with the inner diameter of the drill guide mounted in surgical guide 52 or the diameter of the holes (such as 63) in the block material.

In an embodiment where the drill guide is radiopaque, if swallowed by the patient, an X-ray of the patient may be taken to locate the drill guide.

Figure 6:
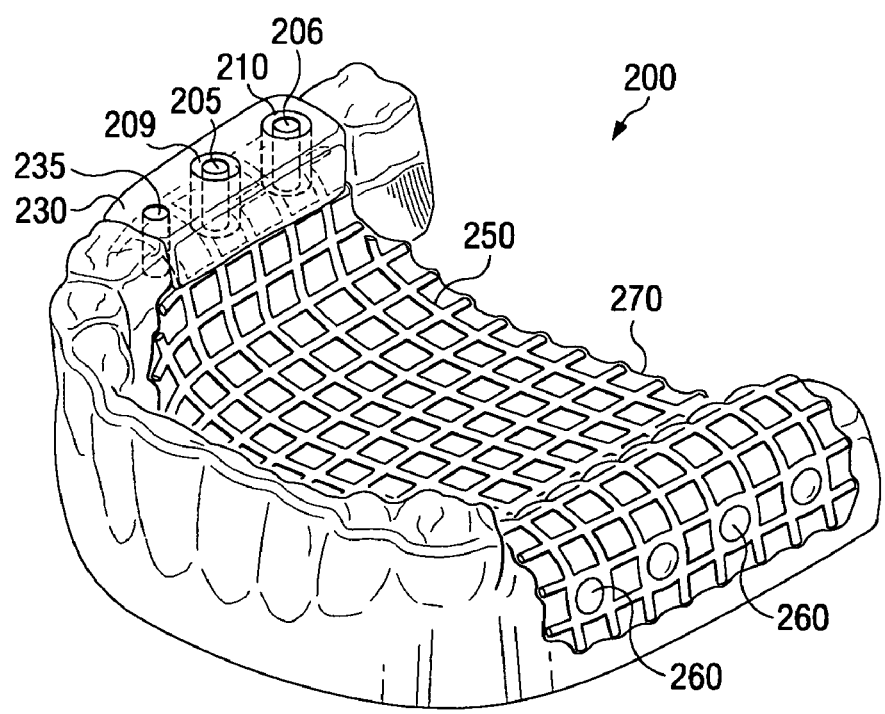
FIG. 6 is a perspective view depicting an alternate embodiment of the implant placement locator and drill guide.

In yet another embodiment, an implant placement locator and drill guide 200 is provided as per FIG. 6. In this embodiment, an implant placement locator such as shown in FIG. 1 at 10 is constructed as previously described. Implant placement locator and drill guide 200 includes moldable grid 250, radiopaque marker 260 and moldable sheet 270. The implant placement locator also includes block material 230 affixed to the surface of moldable sheet 270. Holes 205 and 206 are drilled in block 230 or the block is formed around the drill orientation guide as previously described. Drill orientation guide 210 is rigidly affixed within hole 206 by an epoxy or suitable dental acrylic adhesive. Block material 230 is formed with a suitable acrylic resin placed in the interstitial spaces between teeth or other gaps formed in dental structures. Block material 230 can include holes 235 and 205. In a preferred embodiment all holes are maintained in a generally parallel orientation. In other preferred embodiments, parallelism is not required.

Radiopaque markers 260 are fixed within moldable grid 250. In an alternative embodiment, the drill orientation guide can be a radiopaque material and serve as a radiopaque marker. The preferred embodiment of FIG. 6 allows the advantages of surgical planning using the grid and radiopaque markers in conjunction with radiographs as well as the advantages of the surgical guide provided by the drill guides.

FIG. 10 illustrates a radiograph showing implant placement locator 10 in place on the patient's dental ridge 42 and further shows the final placement of dental implants 44 made pursuant to each drill hole 32 as identified by markers 20.

The embodiments have been described in detail with particular reference to certain preferred embodiments thereof, but it will be understood that variations and modifications can be effected within the scope of the embodiments, especially to those skilled in the art.

The invention claimed is:

1. An implant placement locator for indexing radiographic locations of dental structures in a patient's mouth comprising:
 a moldable thermoplastic indexing grid;
 the indexing grid including a set of open spaces at predetermined intervals;
 a spheroid shaped radiopaque marker located in at least one open space in the set of open spaces;
 a stent structure supporting the indexing grid and the radiopaque marker; and
 whereby the stent structure is molded to the shape of a set of features in the patient's mouth and the radiopaque marker provides a reference point for the dental structures.

2. The implant placement locator of claim 1 wherein the radiopaque marker relates a radiographic image of the dental structure to a location on the patient's dental ridge.

3. The implant placement locator of claim 1 wherein the indexing grid contains a radiopaque wire.

4. The implant placement locator of claim 1 wherein the indexing grid is visibly opaque.

5. The implant placement locator of claim 1 wherein the indexing grid is radiotransparent.

6. The implant placement locator of claim 1 wherein the indexing grid is a light curable plastic.

7. The implant placement locator of claim 1 wherein the radiopaque marker is metallic.

8. The implant placement locator of claim 1 wherein the set of features is selected from a mandible, a maxilla, and a dental palate.

9. The implant placement locator of claim 1 wherein the stent structure is a thermoplastic material.

10. The implant placement locator of claim 1 wherein the indexing grid has rectangular units.

11. The implant placement locator of claim 1 wherein the indexing grid has non-rectangular units.

12. The implant placement locator of claim 1 wherein the indexing grid has grid units of between about 1 mm and about 10 mm.

13. An implant placement locator for guiding the placement of dental implants in a patient's mouth comprising:
a radiolucent moldable grid having a grid spacing;
a set of radiopaque markers located at indexed intervals within the grid spacing of the moldable grid;
a plastic layer supporting the moldable grid and the radiopaque marker; and
whereby the plastic layer is shaped to conform to a set of features in the patient's mouth and the set of radiopaque markers provides a radiographic relationship between the location of the set of radiopaque markers and a dental feature in the patient's mouth.

14. The implant placement locator of claim 13 wherein the moldable grid is a thermoplastic material.

15. The implant placement locator of claim 13 wherein the moldable grid is an ultraviolet curable material.

16. The implant placement locator of claim 13 wherein the radiopaque marker has a diameter ranging from about 1.0 mm to about 4.0 mm.

17. The implant placement locator of claim 13 wherein the radiopaque marker is stainless steel.

18. The implant placement locator of claim 13 wherein at least one radiopaque marker of the set of radiopaque markers is generally spherical.

19. The implant placement locator of claim 13 wherein the dental feature is a bone.

20. The implant placement locator of claim 13 wherein the dental feature is a tooth.

21. The implant placement locator of claim 13 wherein the plastic layer is transparent.

22. The implant placement locator of claim 13 wherein the plastic layer is colored.

23. The implant placement locator of claim 13 wherein the plastic layer is ultraviolet light curable.

24. The implant placement locator of claim 13 wherein the set of features is selected from a mandible, a maxilla, and a dental palate.

25. An implant placement locator for guiding the placement of dental implants in a patient's mouth comprising:
a visible radiolucent moldable grid layer comprising a moldable grid having a grid spacing;
a spheroid shaped radiopaque marker attached to the visible radiolucent moldable grid layer;
a bonding layer which stabilizes the radiopaque marker on the visible radiolucent moldable grid layer; and
whereby the moldable grid is configured to cover a dental feature in the patient's mouth and the radiopaque marker indexes the dental feature within the grid spacing of the moldable grid.

26. The implant placement locator of claim 25 wherein the moldable grid relates the radiopaque marker to the oral tissue of a patient, thereby indexing existing oral structures to the radiopaque marker.

27. The implant placement locator of claim 25 wherein the radiopaque marker is metallic.

28. The implant placement locator of claim 25 wherein the bonding layer comprises a plastic sheet which is transparent and moldable by heat treatment.

29. The implant placement locator of claim 25 wherein the bonding layer comprises a vacuum formed plastic sheet.

30. The implant placement locator of claim 25 wherein the radiopaque marker is fused to the moldable grid by heat.

31. The implant placement locator of claim 25 further comprising a concentrically aligned positioning means fixed with respect to the moldable grid layer and the bonding layer for directing a drilling procedure.

32. The device of claim 25 wherein the moldable grid layer and bonding layer include a hole for location for a surgical procedure.

33. The device of claim 32 further comprising a drill orientation tube concentrically affixed to the hole.

34. The device of claim 33 further comprising a drill spacer cylinder rotationally disposed within the drill orientation tube.

35. The device of claim 34 wherein the drill orientation tube is directed at a predetermined dental feature.

* * * * *